United States Patent
Holder et al.

(10) Patent No.: US 6,589,332 B1
(45) Date of Patent: Jul. 8, 2003

(54) METHOD AND SYSTEM FOR MEASURING POLYCRYSTALLINE CHUNK SIZE AND DISTRIBUTION IN THE CHARGE OF A CZOCHRALSKI PROCESS

(75) Inventors: John D. Holder, Lake St. Louis, MO (US); Steven Joslin, St. Peters, MO (US); Hariprasad Sreedharamurthy, Maryland Heights, MO (US); John Lhamon, St. Peters, MO (US)

(73) Assignee: MEMC Electronic Materials, Inc., St. Peters, MO (US)

( * ) Notice: Subject to any disclaimer, the term of this patent is extended or adjusted under 35 U.S.C. 154(b) by 0 days.

(21) Appl. No.: 09/419,151

(22) Filed: Oct. 15, 1999

Related U.S. Application Data (60) Provisional application No. 60/106,824, filed on Nov. 3, 1998.

(51) Int. Cl.[7] .................................................. C30B 15/00
(52) U.S. Cl. ........................................ 117/14; 382/206
(58) Field of Search ..................... 117/11, 932, 14; 382/190, 195, 192, 206, 224, 225, 228

(56) References Cited

U.S. PATENT DOCUMENTS

| | | | | |
|---|---|---|---|---|
| 4,249,988 A | * | 2/1981 | Lavigna et al. | 156/605 |
| 4,653,109 A | * | 3/1987 | Lemelson et al. | 382/34 |
| 4,831,641 A | | 5/1989 | Niemi | 377/53 |
| 4,962,425 A | * | 10/1990 | Rea | 358/139 |
| 5,018,854 A | | 5/1991 | Rioux | 356/376 |
| 5,126,581 A | | 6/1992 | Furuya et al. | 250/574 |
| 5,349,624 A | | 9/1994 | Warren et al. | 378/43 |
| 5,356,751 A | * | 10/1994 | Cairncross et al. | 430/253 |
| 5,455,675 A | | 10/1995 | Witt et al. | 356/336 |
| 5,588,993 A | | 12/1996 | Holder | 117/13 |
| 5,625,412 A | * | 4/1997 | Aciu et al. | 348/222 |
| 5,814,148 A | | 9/1998 | Kim et al. | 117/13 |
| 5,815,608 A | * | 9/1998 | Lange et al. | 382/312 |
| 5,846,318 A | | 12/1998 | Javidi | 117/14 |
| 5,877,935 A | | 3/1999 | Sato et al. | 361/502 |
| 6,013,915 A | * | 1/2000 | Watkins | 250/341.1 |
| 6,175,644 B1 | * | 1/2001 | Scola et al. | 382/141 |
| 6,175,652 B1 | * | 1/2001 | Jacobson et al. | 382/216 |

FOREIGN PATENT DOCUMENTS

| | | | | |
|---|---|---|---|---|
| DE | 41 13 093 A1 | 10/1991 | | B07B/1/18 |
| DE | 42 07 750 A1 | 10/1992 | | C30B/15/02 |
| EP | 0 611 160 A2 | 8/1994 | | B07C/5/10 |
| GB | 2 246 230 A | 1/1992 | | B07C/5/12 |

OTHER PUBLICATIONS

Brian H. Kaye, Characterization of Powders and Aerosols, Chapter 2, pp. 21–55, 1999. (Stamped in STIC at PTO Jul. 28, 1999).*
W. Zulehner, et al., Crystals Growth, Properties, and Applications 8, Silicon Chemical Etching, 1982, 4 pages.
F. Shimura, Semiconductor Silicon Crystal Technology, pp. 116–121, Academic Press, Inc. (San Diego, CA 1989).
W. O'Mara, Handbook of Semiconductor Silicon Technology, Noyes Publications, pp. 33–93.

* cited by examiner

Primary Examiner—Benjamin L. Utech
Assistant Examiner—Matthew Anderson
(74) Attorney, Agent, or Firm—Senniger, Powers, Leavitt & Roedel (57) ABSTRACT

A method and system for determining polycrystalline silicon chunk size for use with a Czochralski silicon growing process. Polycrystalline silicon chunks are arranged on a measuring background. A camera captures an image of the chunks. An image processor processes the image and determines the dimensions of the chunks based on the captured image. A size parameter associated with the chunks is determined.

12 Claims, 8 Drawing Sheets

METHOD AND SYSTEM FOR MEASURING POLYCRYSTALLINE CHUNK SIZE AND DISTRIBUTION IN THE CHARGE OF A CZOCHRALSKI PROCESS

CROSS-REFERENCE TO RELATED APPLICATION

This application claims the benefit of U.S. provisional application Ser. No. 60/106,824, filed Nov. 3, 1998, the entire disclosure of which is incorporated herein by reference.

BACKGROUND OF THE INVENTION

This invention relates generally to improvements in silicon crystal growth processes and, particularly, to a vision system and method for measuring the size and size distribution of polycrystalline chunks for charging a Czochralski silicon crystal growth process.

Single crystal, or monocrystalline, silicon is the starting material in most processes for fabricating semiconductor electronic components. Crystal pulling machines employing the Czochralski process produce the majority of single crystal silicon. Briefly described, the Czochralski process involves melting a charge of high-purity polysilicon, or polycrystalline silicon, in a quartz crucible located in a specifically designed furnace. Typically, the charge is made up of irregularly-shaped chunk polycrystalline silicon prepared by, for example, the Siemens process. The preparation and characteristics of chunk polysilicon are further detailed in F. Shimura, *Semiconductor Silicon Crystal Technology*, pages 116–121, Academic Press (San Diego Calif., 1989) and the references cited therein. After the polysilicon charge in the crucible is melted, a crystal lifting mechanism lowers a seed crystal into contact with the molten silicon. The mechanism then withdraws the seed to pull a growing crystal from the silicon melt.

A substantial concern in the production of single crystal ingots by the Czochralski process is the need to prevent the formation of dislocations, voids, or other defects in the single crystal lattice structure. In general terms, dislocations are undesirable faults in crystal geometry resulting from thermal shock, vibration or mechanical shock, internal strain due to regional cooling rate differences, solid particles in the melt at the crystal growth interface, gas bubbles trapped within the melt, surface tension effects or the like. Once generated, dislocations degrade the uniformity of the crystal's electrical characteristics and permit the attachment of impurities to the single crystal. Further aggravating the problem is that any localized defect or dislocation in the single crystal typically spreads and often renders much of an ingot unusable. Therefore, it is desirable to grow single crystal ingots having the greatest possible zero dislocation length. Ideally, the entire usable portion of an ingot would have zero dislocations.

Although presently available Czochralski growth processes have been satisfactory for growing single crystal silicon useful in a wide variety of applications, further improvements are still desired. In particular, the polysilicon chunks used to charge the crucible have different shapes and sizes because they are typically obtained by manually breaking U-shaped rods of polycrystalline silicon, grown from a chemical vapor deposition process. Due to the brittle nature of polycrystalline silicon and the manual breaking operation, the chunks do not have a fixed shape. Rather, the chunks consist of small and large pieces with a combination of sharp, blunt, and round edges. The shape and size of the chunks, as well as the size distribution of the chunks, can vary widely depending on the producer of the polycrystalline silicon. The sizes of the polysilicon chunks can even vary among lots produced by the same producer.

The size distribution of chunks plays a significant role in the melting behavior of the charge and in the likelihood that dislocations or other defects might appear in the final ingot. For example, the size distribution of polycrystalline silicon chunks influences contributors to loss of structure during the growth process such as splashing rim oxide, flaking, bridging, and quartz pieces. Presently, polycrystalline silicon producers do not measure the size of the chunks or their size distribution on a regular basis. At most, producers of polysilicon use a ruler to measure the length and breadth of the chunks. Unfortunately, this method of measuring chunk size is time consuming, laborious, and inaccurate. Knowledge of size data would facilitate a determination of optimum chunk sizes and size distributions, and, consequently, would improve efficiency and throughput.

For these reasons, an improved system and method for the measuring the average size and the size distribution of polycrystalline silicon chunks for use in the Czochralski process is desired.

SUMMARY OF THE INVENTION

The invention meets the above needs and overcomes the deficiencies of the prior art by providing an improved system and method for analyzing the average size and the size distribution of polycrystalline silicon chunks. This is accomplished by an image processor or vision system that is more efficient and less time consuming than the prior art. Advantageously, the present invention provides measurements of a range of parameters including average diameter, perimeter size, surface area, aspect ratio, and the size distribution of the chunks. In addition, the system is economically feasible and commercially practical, and the method can be carried out efficiently and economically.

Briefly described, a method embodying aspects of the invention permits a determination of polycrystalline silicon chunk size for use with a Czochralski silicon growing process. The method includes arranging one or more polycrystalline silicon chunks on a measuring background that provides an image contrast between the polycrystalline silicon chunks and the measuring background. An image of the polycrystalline silicon chunks on the measuring background is generated with a camera. The image has a plurality of pixels and each pixel has a value that represents an optical characteristic of the generated image. The image is processed as a function of the pixel values to detect edges in the image. According to the method, the detected edges are grouped to define one or more objects in the image corresponding to the polycrystalline silicon chunks. The method further includes determining a dimension of each defined object. A size parameter associated with the polycrystalline silicon chunks on the measuring background is then determined as a function of the determined dimensions of the defined objects.

Another embodiment of the invention is a system for determining polycrystalline silicon chunk size for use with a Czochralski silicon growing process. The system includes a measuring background that is positioned to support one or more polycrystalline silicon chunks. The measuring background is such that it provides an image contrast between the polycrystalline silicon chunks and the measuring background. The system also includes a camera for generating an image of the polycrystalline silicon chunks on the measuring background. The image generated by the camera has a plurality of pixels and each pixel has a value representative of an optical characteristic of the generated image. An image processor processes the generated image as a function of the pixel values to detect edges in the image. The image processor groups the detected edges to define one or more objects in the image corresponding to the polycrystalline silicon chunks and then determines a dimension of each defined object. The image processor also determines a size parameter associated with the polycrystalline silicon chunks on the measuring background as a function of the determined dimensions of the defined objects.

Alternatively, the invention may comprise various other systems and methods.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION OF PREFERRED EMBODIMENTS

Figure 1:
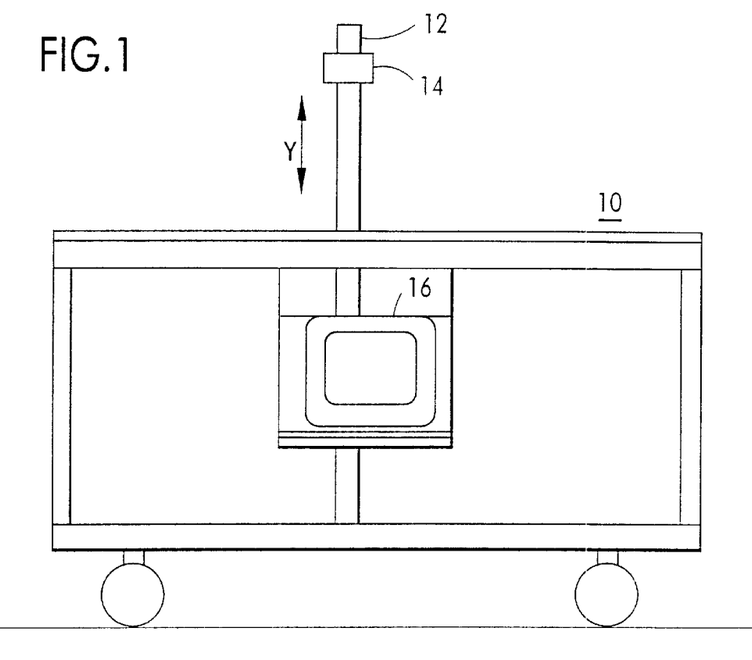
FIG. 1 is a schematic of a front view of a system for measuring polycrystalline silicon chunk size according to a preferred embodiment of the invention.
Figure 2:
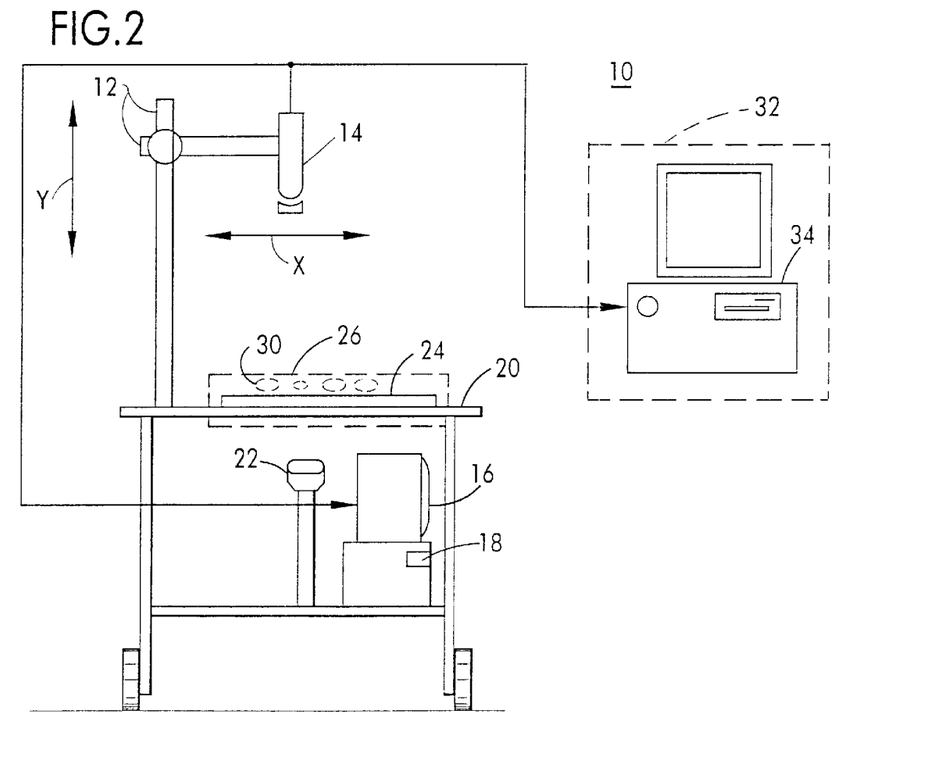
FIG. 2 is a schematic of a side view of a system for measuring polycrystalline silicon chunk size according to a preferred embodiment of the invention.

Referring now to the drawings, FIGS. 1 and 2 show a system for measuring polycrystalline silicon chunk size for use with a Czochralski single crystal growing process. According to a typical growth process, a quantity of chunk polycrystalline silicon, or polysilicon, is charged to a crucible. A heater surrounding the crucible melts the charge to form a silicon melt from which a single crystal is pulled. Commonly assigned U.S. Pat. Nos. 5,588,993 and 5,814, 148, the entire disclosures of which are incorporated herein by reference, describe suitable methods of preparing a polycrystalline silicon charge. Once loaded, the crucible is placed in a crystal growing apparatus, the heater of which melts the polysilicon to form the silicon melt. A susceptor situated on a movable pedestal associated with the crucible drive unit supports the crucible. The pedestal is positioned such that the bottom of the crucible is near the top of the heater and gradually lowered into the space inside the heater. The speed at which the crucible drive unit lowers the crucible into the heater, as well as other factors (e.g., heater power, crucible rotation, and system pressure), affects the melting of the polysilicon charge.

As described above, the size distribution of the polysilicon chunks plays a significant role in the melting behavior of the charge, which, in turn, affects the possibility of dislocations or other defects appearing in the final ingot. The size distribution affects splashing rim oxide, flaking, bridging, quartz pieces, and other factors that contribute to a loss of structure during the growth process. According to the present invention, the system of FIGS. 1 and 2 facilitates a new method for determining an average size and size distribution of the polycrystalline chunks. This method is less time consuming and is amenable to a more detailed data analysis than conventional techniques. Further, this size information may be used to optimize the choice of polycrystalline silicon for use in charging a Czochralski growth process.

The system of the present invention includes a portable light table 10 with an adjustable arm 12, a digital camera 14, and a video monitor 16. The digital camera 14 is attached to the adjustable arm 12 of the light table 10 at a horizontal position X and a vertical position Y. Since arm 12 is adjustable, an operator can vary the X and/or Y positions of camera 14. As schematically shown in FIG. 2, light table 10 comprises a top surface 20 that is illuminated by a light source 22, also referred to as an illumination source. Although FIG. 2 depicts the light source 22 as a light that shines upward to the top surface 20, other lighting configurations may be used with the system and method of present invention. A high purity polyethylene sheet 24 is placed on top surface 20. The polyethylene sheet 24 and top surface 20 constitute a measuring background 26. The operator, wearing high purity gloves, then places polycrystalline silicon chunks 30 piece by piece onto polyethylene sheet 24. Preferably, the operator selects the chunks 30 from a single lot, typically in a bag, and arranges the chunks 30 in a single layer such that adjacent chunks do not touch each other. With light table 10 illuminated, digital camera 14 acquires an image of chunks 30 positioned on the measuring background 26.

As shown in FIG. 2, in one embodiment of the invention, camera 14 communicates the digital images of chunks 30 that it acquires to an image processor 32 for analysis. The image processor 32 preferably comprises a computer 34 executing image processing software such as, for example, IMAGE-PRO® software by Media Cybernetics. The acquired chunk images may also be communicated to a separate video monitor that may or may not be connected to the image processor. The embodiment shown in FIG. 2 shows video monitor 16 as separate and distinct from image processor 32, but it should be understood that image processor 32 could further comprise video monitor 16 (i.e., images may be displayed on a monitor associated with computer 34). In FIG. 2, video monitor 16 is also connected to a video cassette recorder (VCR) 18 for recording the images acquired by camera 14.

Figure 3:
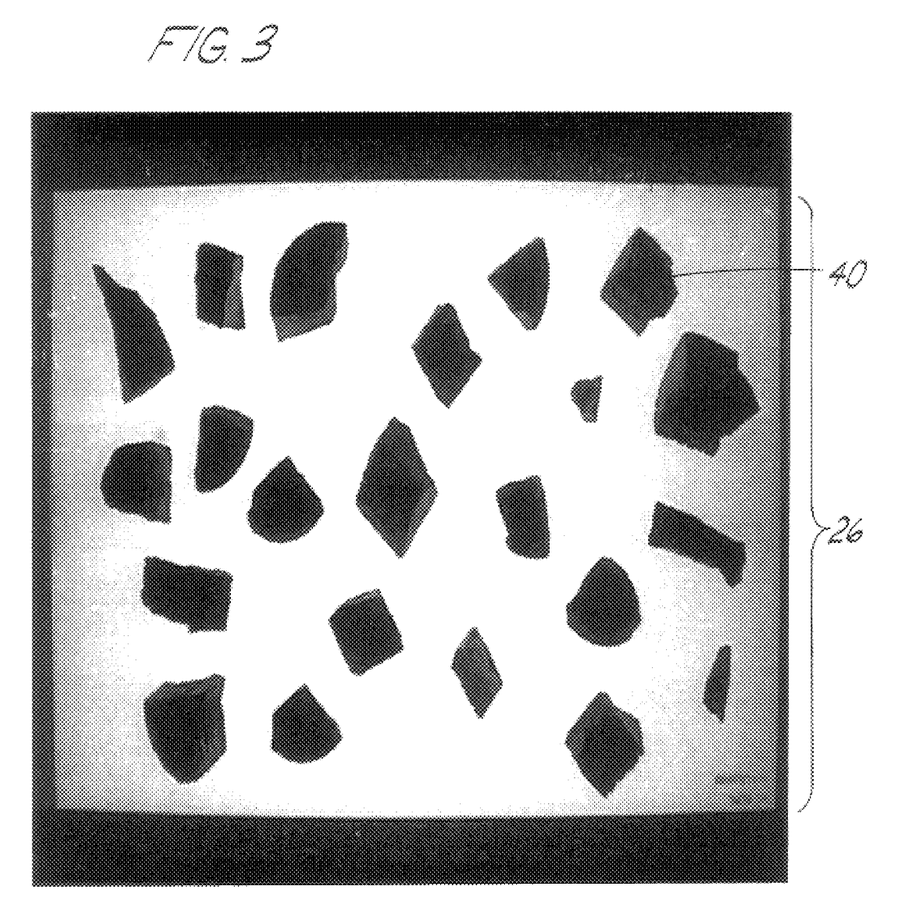
FIG. 3 is an exemplary illustration of a digital image of Type 1 silicon chunks.
Figure 4:
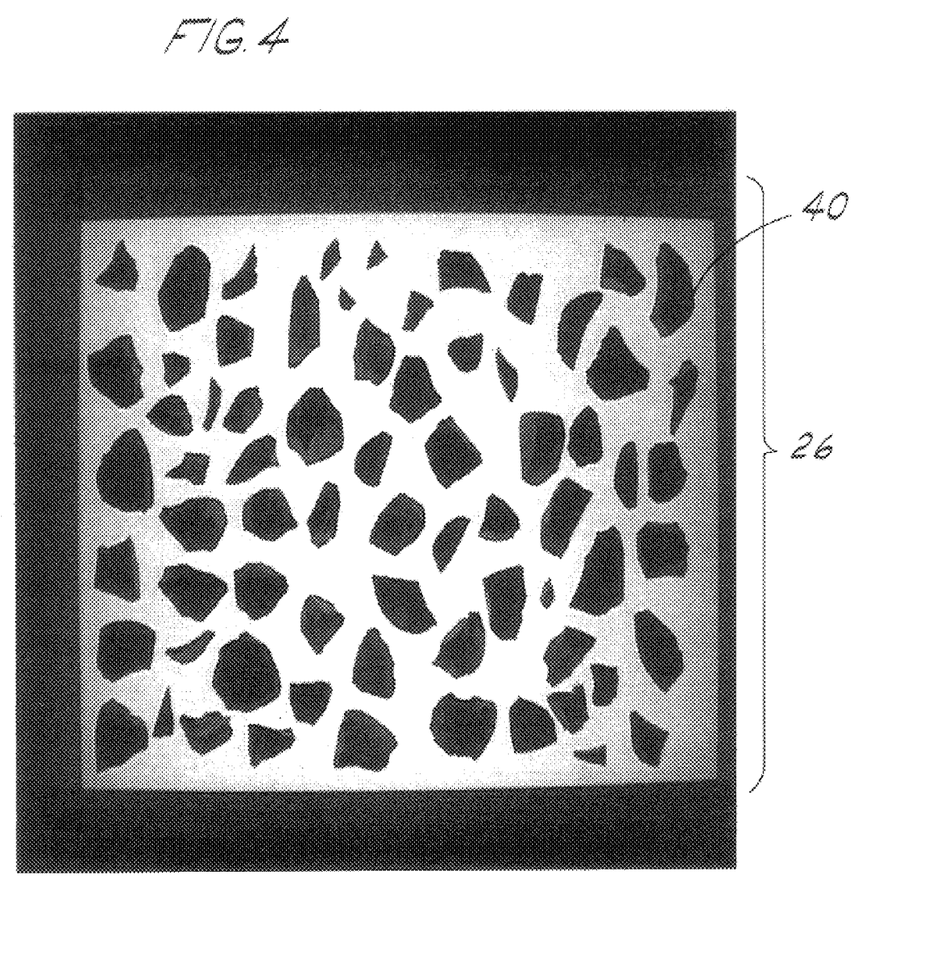
FIG. 4 is an exemplary illustration of a digital image of Type 2 silicon chunks.
Figure 5:
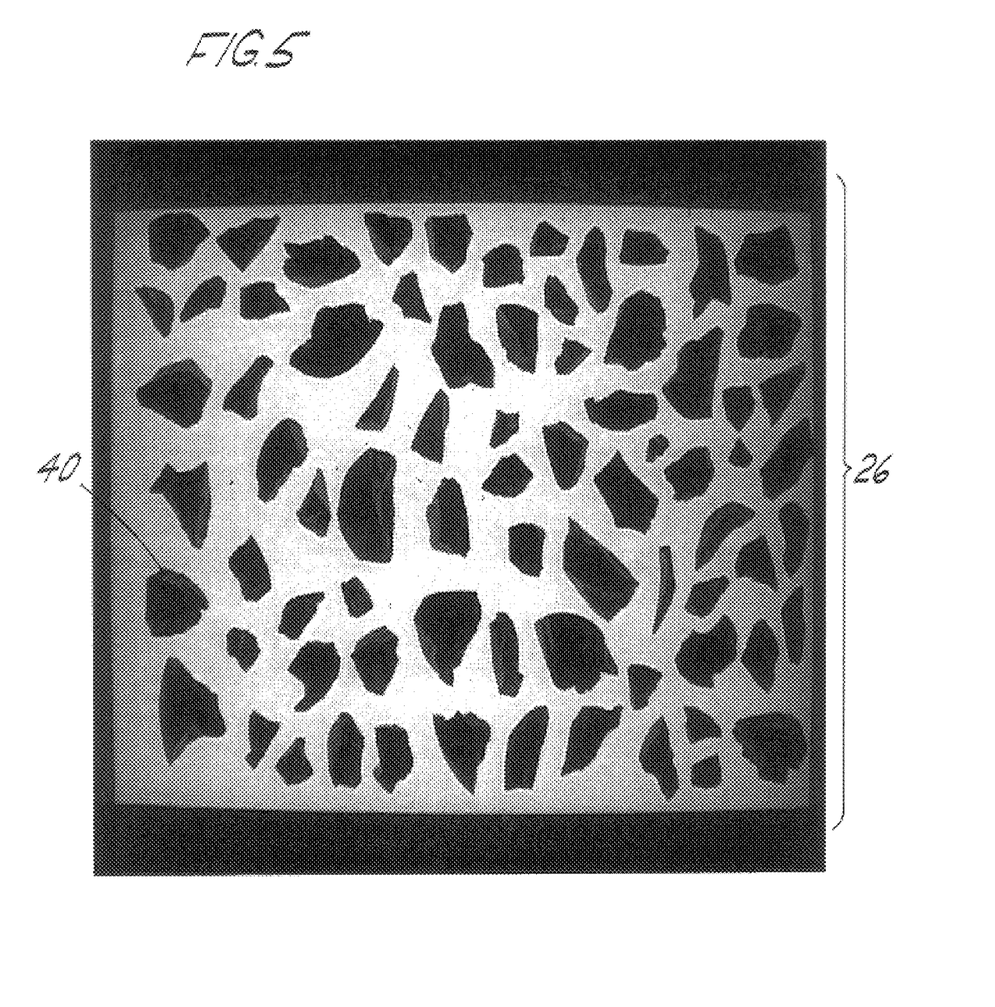
FIG. 5 is an exemplary illustration of a digital image of Type 3 silicon chunks.

FIGS. 3–5 show exemplary digital images of chunks provided by different producers of polycrystalline silicon. As shown in FIGS. 3–5, the polycrystalline silicon chunks are arranged on measuring background 26 such that none of the chunks 30 touch an adjacent chunk. Light source 22 (see FIG. 2) then illuminates illumination background 26. The back-lighting effect generated thereby causes the polycrystalline silicon chunks 30 to appear as silhouettes 40 against measuring background 26.

Advantageously, and as can be seen in FIGS. 3–5, the cross-sectional area of each chunk silhouette 40 provides an approximation of chunk size. Further, the sharp contrast generated by the difference between chunk silhouettes 40 and measuring background 26 allows image processor 32 to easily detect chunk edges and compute the cross-sectional area of each chunk silhouette 40. In one embodiment, image processor 32 defines a bounding box around each chunk silhouette 40. The dimensions of the box approximate the area of the chunk 30. Once image processor 32 has computed the cross-sectional area of each chunk silhouette 40, image processor 32 (or another processor or software package) can determine other size parameters such as, for example, the average chunk size, the standard deviation of the size of the chunks, the distribution of chunks as a function of chunk size, and other size or shape parameters useful in determining which chunks to use in charging a Czochralski silicon growth process.

It should be understood that the method and system of the present invention may be utilized with other techniques for determining or estimating chunk size. For example, images taken from multiple angles may be used to determine chunk volume rather than chunk cross-sectional area. It is also possible to use a single image and an image processor that interprets contour data or other information obtained from that image to determine chunk volume or surface area in addition to (or instead of) cross-sectional area. It is further possible to acquire an image with a standard (non-digital) camera and thereafter digitize and process the acquired image.

Figure 6:
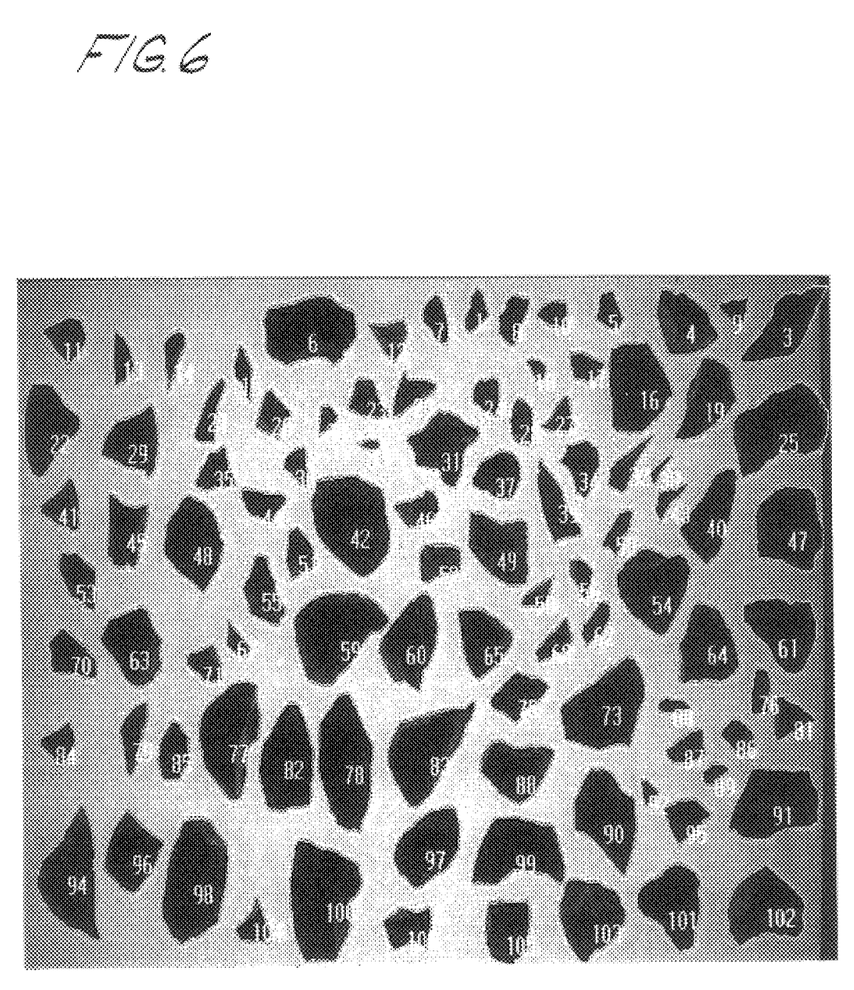
FIG. 6 is an exemplary illustration of a digital image of silicon chunks undergoing analysis by the system of FIGS. 1 and 2.

FIG. 6 illustrates an exemplary digital image as it is analyzed by image processor 32. Each chunk is analyzed and numbered. As described above, image processor 32 determines the cross-sectional area of each enumerated chunk as well as collective data relating to all of the chunks on measuring background 26.

Table I summarizes the mean area, the standard deviation, and the size distribution for each of the three types of polycrystalline silicon chunks shown in FIGS. 3–5. In the example shown in Table I, size distribution is defined as the standard deviation divided by the mean area. It should be noted, however, that size distribution may be defined in terms of other size data. The chunks shown in FIG. 3 are referred to as Type 1 polycrystalline silicon chunks. The chunks shown in FIG. 4 are Type 2 polycrystalline silicon chunks. Finally, the chunks shown in FIG. 5 are Type 3 polycrystalline silicon chunks.

TABLE I

| Type | Mean Area, Inches | Standard Deviation | Size Distribution |
| --- | --- | --- | --- |
| Type 1 | 7.04 | 2.87 | 0.41 |
| Type 2 | 2.73 | 1.52 | 0.54 |
| Type 3 | 3.08 | 2.08 | 0.67 |

In this example, a chunk measuring system of the present invention determined the average size of the chunks, the standard deviation of the chunks, and the size distribution of the chunks. As shown in Table I and illustrated in FIG. 3, Type 1 chunks have a much larger average size than Type 2 or Type 3 chunks. Further, as illustrated in FIGS. 4 and 5, and as shown in Table I, although Type 2 and Type 3 chunks have generally comparable sizes, the size distribution is narrower for Type 2 chunks than for Type 3 chunks.

Figure 7:
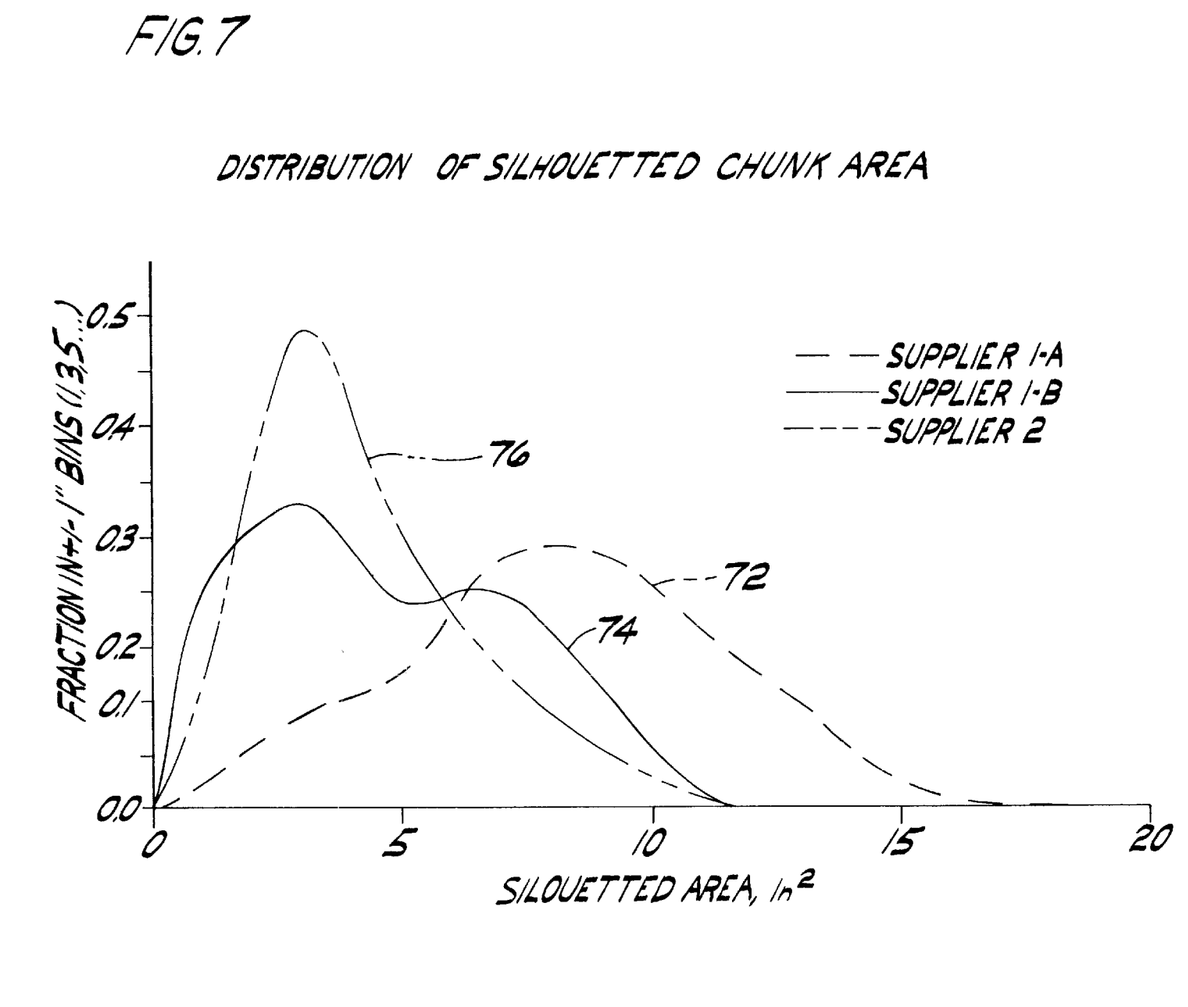
FIG. 7 is an exemplary graph of the size distribution of silicon chunks versus the silhouetted area of the chunks as determined by the system of FIGS. 1 and 2.
Figure 8:
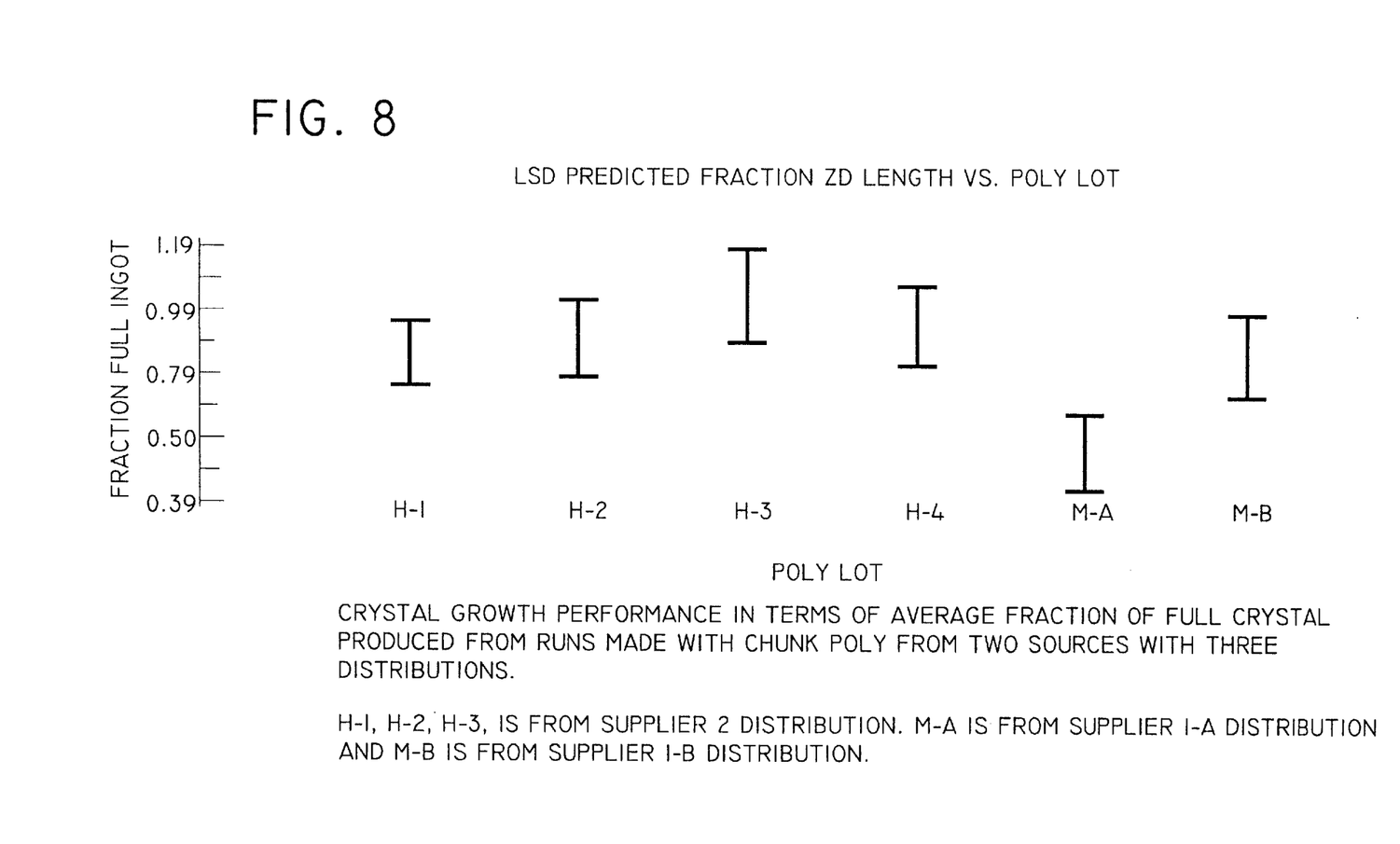
FIG. 8 is an exemplary graph of the fraction of single crystal silicon having zero dislocations versus polycrystalline chunk lot.

Referring now to FIGS. 7 and 8, and as explained above, knowledge of average chunk size in general, and chunk size distribution in particular, is helpful in choosing the chunks for charging a Czochralski silicon growth process. As shown in FIG. 7, the size distribution of polycrystalline silicon chunks from three suppliers is plotted as a function of the cross-sectional area of the chunks. The size distribution curve 72 of chunks from Supplier 1-A is relatively flat compared to the size distribution curves 74, 76 of chunks from Supplier 1-B and Supplier 2. Thus, the chunks obtained from Supplier 1-A are similar to the Type 1 chunks shown in FIG. 3 and Table I. On the other hand, the chunks from Supplier 1-B, while smaller on average than the chunks obtained from Supplier 1-A, still have a fairly large size distribution when compared with the chunks obtained from Supplier 2. The chunks obtained from Supplier 1-B are similar to the Type 3 chunks shown in FIG. 5 and Table I.

The horizontal axis of the graph shown in FIG. 7 reflects the number of polycrystalline silicon chunks that fit into ± one square inch odd numbered size categories, also referred to as bins or size bins. For example, all chunks having silhouetted areas between zero and two square inches are counted in the one square inch bin. Similarly, all chunks having silhouetted areas between two and four square inches are counted in the three square inch bin. This process is continued until the area of all of the chunks are counted.

The number of chunks falling into each odd numbered size bin is then divided by the total number of chunks to determine the fraction of the total placed in any given bin. The fraction data is plotted for each odd numbered bin and then a curve is fit to the data as shown in FIG. 7. For example, distribution curve 74 reflects the size distribution for polycrystalline silicon chunks from supplier 1-B. As shown by curve 74, slightly less than 20 percent (0.20) of all of the chunks from supplier 1-B were counted in the five square inch bin. In other words, 20 percent of all chunks from supplier 1-B had a measured silhouetted area between four and six square inches.

FIG. 8 illustrates a statistical benefit of using the present invention to determine chunk size data. As explained above, it is normally desirable to grow single crystal silicon having the greatest zero dislocation length possible. FIG. 8 depicts predicted crystal growth performance, in terms of zero dislocation length, as a function of polycrystalline silicon chunk lot. Referring first to the horizontal axis of FIG. 8, H-1 through H-4 are four different lots of polycrystalline silicon from Supplier 2. M-A is a lot from supplier 1-A, and M-B is a lot from supplier 1-B. The vertical axis reflects predicted crystal growth performance with 95 percent error bars. For example, roughly 90 percent (the middle of the error bar) of single crystal ingots grown from polycrystalline silicon chunks from lots having the same characteristics as lot H-1 would be grown with zero dislocations. The 95 percent error bars reflects the statistical confidence of the performance predictions.

A substantial overlap in the 95 percent error bars between suppliers indicates that, as a statistical matter, the differences between lots may not be observed in terms of the zero dislocation length of the final single crystal ingots produced. Data from multiple lots and from multiple suppliers can be gathered so that optimum polycrystalline silicon chunk size information may be determined. This information is helpful in eliminating at least two types of errors. First, it reduces the likelihood that a useable lot of polycrystalline silicon will be discarded. Second, and equally important, it allows users to discard lots of polycrystalline silicon that will likely produce poor quality single crystal silicon.

This method for determining the size and size distribution of polycrystalline silicon chunks holds distinct advantages over existing measurement techniques. The method lends itself to making use of all the analytical tools that are available with image processing software (e.g., IMAGE-PRO® Software) for the data analysis. Advantageously, the present invention provides measurements of a range of parameters including average diameter, perimeter size, surface area, aspect ratio, and the size distribution of the chunks.

Figure 9:
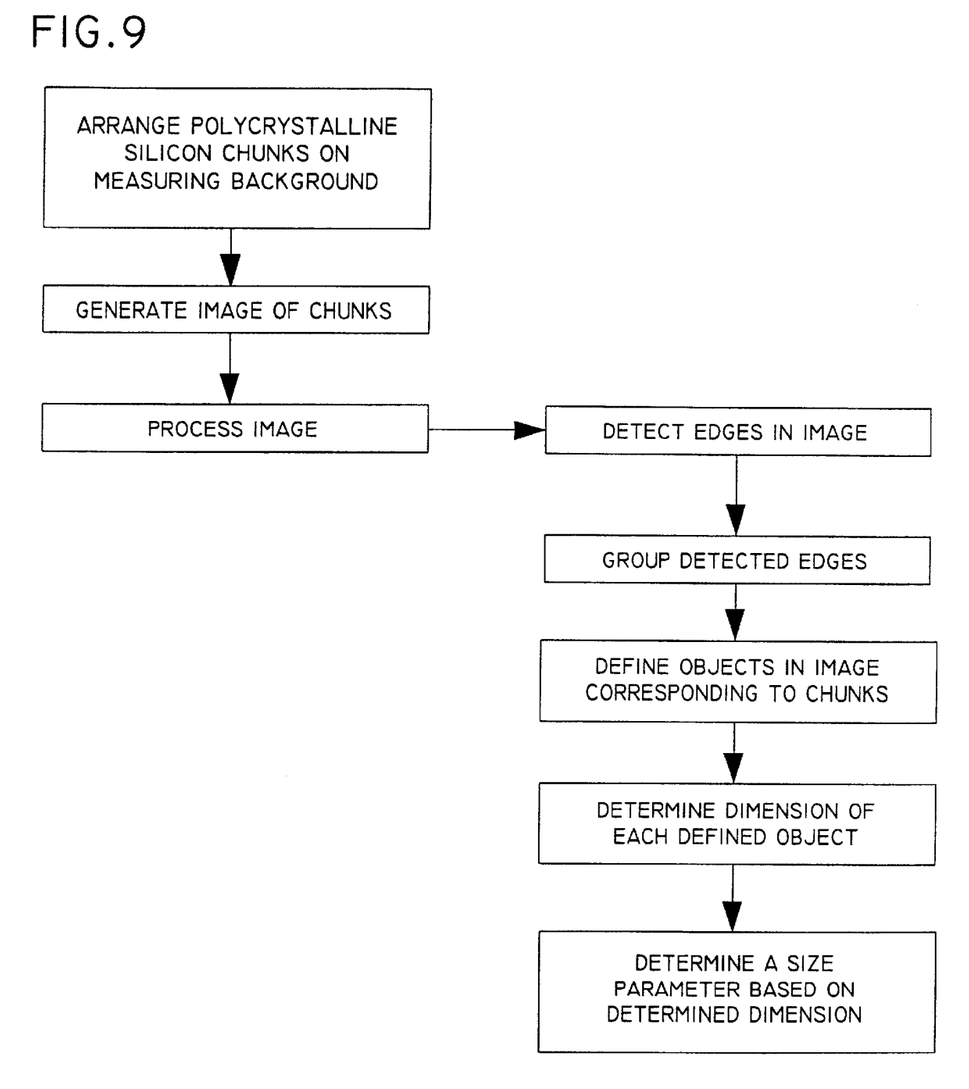
FIG. 9 is a flow chart that illustrates a method for determining polycrystalline silicon chunk size information according to the invention.

Referring now to FIG. 9 in connection with FIGS. 1 and 2, in operation the invention comprises a method for determining polycrystalline chunk size for charging a Czochralski crystal growing process. One or more polycrystalline chunks 30 are arranged on measuring background 26 so as to produce an image contrast between polycrystalline chunks 30 and measuring background 26. Camera 14 generates an image of polycrystalline chunks 30. The generated image is comprised of a plurality of pixels; each pixel has a value representative of an optical characteristic of the generated image. For example, the optical characteristic may be a gray scale value. Image processor 32 processes the generated image as a function of the pixel values to detect edges in the image. Image processor 32 groups the detected edges to define one or more objects in the image corresponding to polycrystalline chunks 30. Image processor 32 then determines a dimension of each defined object. Finally, image processor 32 determines a size parameter associated with polycrystalline chunks 30 as a function of the determined dimensions of the defined objects.

The size parameter may reflect size information relating to individual polycrystalline chunks 30 and/or all of the polycrystalline chunks 30 arranged on measuring background 26. For example, the size parameter may be a measurement indicative of the cross-sectional area, perimeter size, aspect ratio, or surface area of each polycrystalline chunk 30. Alternatively, the size parameter may be a measurement indicative of the average diameter or size distribution of all of the polycrystalline chunks 30 being analyzed.

The present invention may be used to the advantage of polycrystalline silicon suppliers as well as single crystal ingot manufacturers. Polycrystalline silicon suppliers can use the present invention to produce packages of polycrystalline silicon chunks having the most desirable size characteristics for a given customer. Single crystal ingot manufacturers can use the present invention to optimize the crystal growth process by charging the Czochralski silicon growth process with polycrystalline chunks having ideal or near ideal size characteristics.

In view of the above, it will be seen that the several objects of the invention are achieved and other advantageous results attained.

As various changes could be made in the above constructions and methods without departing from the scope of the invention, it is intended that all matter contained in the above description or shown in the accompanying drawings shall be interpreted as illustrative and not in a limiting sense.

What is claimed is:

1. A method for determining polycrystalline silicon chunk size for use with a Czochralski silicon growing process, said method comprising the steps of:

arranging polycrystalline silicon chunks on a measuring background, said measuring background providing image contrast between the polycrystalline silicon chunks and the measuring background;

generating an image of the polycrystalline silicon chunks on the measuring background with a camera, said image having a plurality of pixels, each pixel having a value representative of an optical characteristic of the generated image;

processing the image as a function of the pixel values to detect edges in the image;

grouping the detected edges to define one or more objects in the image corresponding to the polycrystalline silicon chunks;

determining a dimension of each defined object;

determining a measurement indicative of a size distribution of the polycrystalline silicon chunks on the measuring background as a function of the determined dimensions of the defined objects; and determining a zero dislocation growth performance of a crystal grown from the polycrystalline silicon chunks as a function of the size distribution.

2. The method of claim 1 further comprising determining a measurement indicative of an average diameter of the polycrystalline silicon chunks.

3. The method of claim 1 further comprising determining a measurement indicative of a perimeter size of each polycrystalline silicon chunk.

4. The method of claim 1 further comprising determining a measurement indicative of a surface area of each polycrystalline silicon chunk.

5. The method of claim 1 further comprising determining a measurement indicative of an aspect ratio of each polycrystalline silicon chunk.

6. The method of claim 1 further comprising determining a measurement indicative of a cross-sectional area of each polycrystalline silicon chunk.

7. The method of claim 1 wherein the measuring background is translucent and further comprising the step of illuminating the measuring background to provide an increased image contrast between the polycrystalline silicon chunks and the measuring background.

8. The method of claim 1 wherein the arranging step further comprises placing each of the polycrystalline silicon chunks on the measuring background such that none of the chunks contacts an adjacent chunk.

9. The method of claim 1 wherein the camera is a digital camera and the generated image is a digital image.

10. A method for use with a Czochralski silicon growing process, said method comprising the steps of:

arranging a plurality of polycrystalline silicon chunks from a lot of polycrystalline silicon chunks on a measuring background, said measuring background providing image contrast between the plurality of polycrystalline silicon chunks and the measuring background;

generating an image of the plurality of polycrystalline silicon chunks on the measuring background with a camera, said image having a plurality of pixels, each pixel having a value representative of an optical characteristic of the generated image;

processing the image as a function of the pixel values to detect edges in the image;

grouping the detected edges to define one or more objects in the image corresponding to the plurality of polycrystalline silicon chunks;

determining a dimension of each defined object;

determining a measurement indicative of a size distribution of the plurality of polycrystalline silicon chunks on the measuring background as a function of the determined dimensions of the defined objects; and determining a predicted crystal growth performance characteristic of a crystal to be grown from the lot of polycrystalline silicon chunks as a function of the determined size distribution.

11. The method of claim 10, wherein determining the predicted crystal growth performance characteristic comprises comparing the determined size distribution to one or more reference size distributions, each of said one or more reference size distributions having a known growth performance characteristic, whereby the predicted crystal growth performance characteristic is substantially similar to the known growth performance characteristic of the one or more reference size distributions most closely matching the determined size distribution.

12. The method of claim 10 further comprising discarding the lot of polycrystalline silicon chunks if the predicted crystal growth performance characteristic indicates that the lot will likely produce poor quality single crystal silicon.

* * * * *